United States Patent
Hanya et al.

(10) Patent No.: US 8,202,710 B2
(45) Date of Patent: Jun. 19, 2012

(54) LACTIC ACID BACTERIUM CAPABLE OF PRODUCING γ-AMINOBUTYRIC ACID

(75) Inventors: Yoshiki Hanya, Chiba (JP); Itsuo Sato, Chiba (JP); Ryo Shimojo, Chiba (JP)

(73) Assignee: Kikkoman Corporation, Chiba (JP)

( * ) Notice: Subject to any disclaimer, the term of this patent is extended or adjusted under 35 U.S.C. 154(b) by 913 days.

(21) Appl. No.: 12/279,266

(22) PCT Filed: Feb. 21, 2007

(86) PCT No.: PCT/JP2007/053223
§ 371 (c)(1),
(2), (4) Date: Aug. 13, 2008

(87) PCT Pub. No.: WO2007/097374
PCT Pub. Date: Aug. 30, 2007

(65) Prior Publication Data
US 2009/0186388 A1    Jul. 23, 2009

(30) Foreign Application Priority Data
Feb. 21, 2006  (JP) .................................. 2006-043836

(51) Int. Cl.
*C12P 13/04*    (2006.01)
*C12N 1/20*    (2006.01)

(52) U.S. Cl. ..................................... 435/106; 435/252.9

(58) Field of Classification Search .................. 435/106, 435/252.9
See application file for complete search history.

(56) References Cited

FOREIGN PATENT DOCUMENTS

| | | |
|---|---|---|
| JP | 2704493 | 8/1995 |
| JP | 2000-210075 | 8/2000 |
| JP | 3426157 | 11/2000 |
| JP | 2002-360289 | 12/2002 |
| JP | 2003-180389 | 7/2003 |
| JP | 2004-187501 | 7/2004 |
| JP | 2004-215529 | 8/2004 |
| JP | 2004-357535 | 12/2004 |
| JP | 2005-065691 | 3/2005 |
| JP | 2005-102559 | 4/2005 |
| JP | 2005-198578 | 7/2005 |
| JP | 2005-312438 | 11/2005 |

OTHER PUBLICATIONS

Chenoll et al., "*Lactobacillus rennini* sp. nov., isolated from rennin and associated with cheese spoilage" *International Journal of Systematic and Evolutionary Microbiology* 56:449-52, 2006.
Database EMBL Accession No. AJ576007, *Lactobacillus rennini* 16S rRNA gene, strain CECT 5922, submitted Jul. 9, 2003.
Higuchi et al., "Exchange of Glutamate and γ-Aminobutyrate in a *Lactobacillus* Strain" *J. Bacteriol*. 179(10):3362-64, 1997.
GenBank Accession No. AB240455, *Lactobacillus halophilus* gene for 16S rRNA, partial sequence, submitted Nov. 4, 2005.
English Language Abstract of JP 2000-308457, published Nov. 7, 2000.
English Language Abstract of JP 7-227245, published Aug. 29, 1995.

*Primary Examiner* — Herbert J Lilling
(74) *Attorney, Agent, or Firm* — Greenblum & Bernstein, P.L.C.

(57) ABSTRACT

The present invention provides a lactic acid bacterium which can produce γ-aminobutyric acid (GABA) even under a coexisting condition of lactic acid and common salt in a medium at time of commencement of culturing, and a method for producing a culture mixture comprising GABA. Specifically, a culture mixture comprising GABA can be obtained by isolating from unrefined soy a lactic acid bacterium, *Lactobacillus rennini* which can produce GABA even under a coexisting condition of lactic acid and common salt in a medium at time of commencement of culturing, and culturing the lactic acid bacterium after inoculating it into a medium containing L-glutamic acid and/or salts thereof.

2 Claims, 1 Drawing Sheet

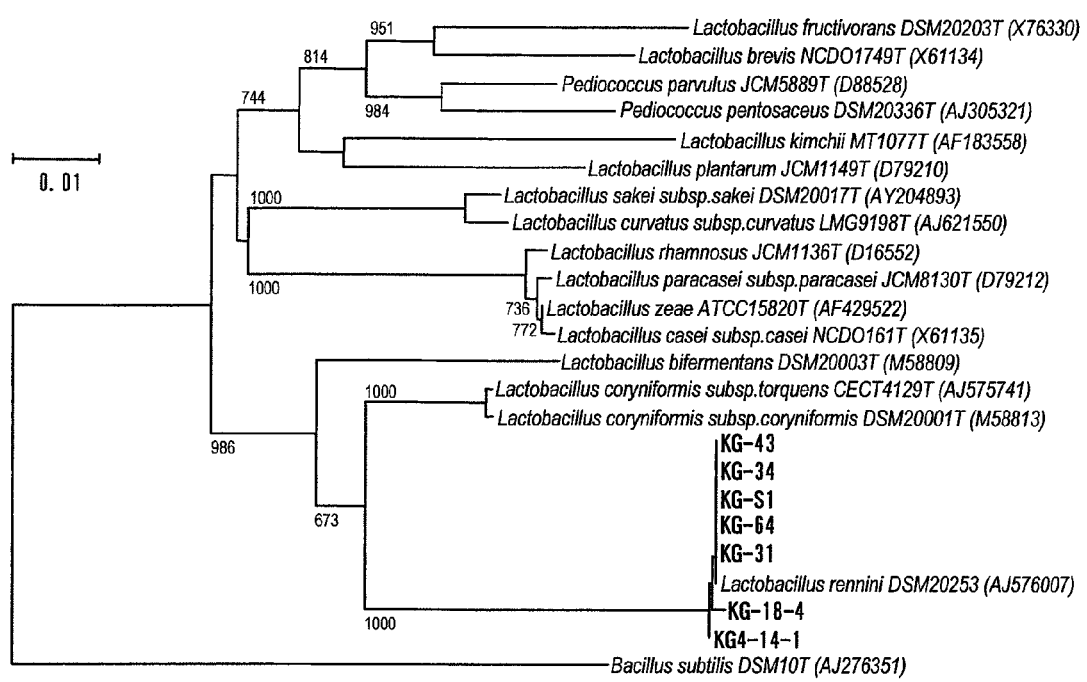

SEQUENCE LISTING

```
<160> NUMBER OF SEQ ID NOS: 2

<210> SEQ ID NO 1
<211> LENGTH: 1526
<212> TYPE: DNA
<213> ORGANISM: Lactobacillus rennini
<220> FEATURE:
<223> OTHER INFORMATION: KG34(NITE BP-177)

<400> SEQUENCE: 1
gtttgatcct ggctcaggac gaacgctggc ggcgtgccta atacatgcaa gtcgcacgca      60
caaccgttaa cctgatcctg cttgcaggtg acgttaatgg acgtgagtgg cggacgggtg     120
agtaacacgt gggtaaccaa ccctgaagcg ggggataacc tttggaaaca gaggctaata     180
ccgcatagtt tatcgcgacc tcctggtcgc aataataaag acggcttcgg ctgtcacttc     240
aggacagacc cgcggcgtat tagctagttg gtgggataaa ggcctaccaa ggcgatgata     300
cgtagccgac ctgagagggt aatcggccac attgggactg agacacggcc caaactccta     360
cgggaggcag cagtagggaa tcttccacaa tggacgcaag tctgatggag caacgccgcg     420
tgagtgaaga agggtttcgg ctcgtaaaac gctgttgttg gagaagaacc gggggtagag     480
taactgttat ccccttgacg gtatccaacc agaaagccac ggctaactac gtgccagcag     540
ccgcggtaat acgtaggtgg caagcgttgt ccggatttat tgggcgtaaa gcgagcgcag     600
gcggtttttt aagtctgatg tgaaagcctt cggcttaacc gaagaagggc atcagaaact     660
gagaagcttg aggacagaaa aggaaagtgg aactccatgt gtagcggtga aatgcgtaga     720
tatatggaag aacaccagtg gcgaaggcgg ctttctggtc tgttactgac gctgaggctc     780
gaaagtatgg ggagcgaaca ggattagata ccctggtagt ccataccgta aacgatgaat     840
gctaagtgtt ggagggtttc cgcccttcag tgctgcagct aacgcattaa gcattccgcc     900
tggggagtac gaccgcaagg ttgaaactca aaggaattga cggggcccg cacaagcggt     960 ggagcatgtg gtttaattcg aagcaacgcg aagaaccta ccaggtcttg acatcctttg    1020
accgctgtcg agagacagtt tgcccttcgg gccaaagtg acaggtggtg catggttgtc    1080
gtcagctcgt gtcgtgagat gttgggttaa gtcccgcaac gagcgcaacc cttatgacta    1140
```

```
gttgccagca tttagttggg cactctagtg agactgccgg tgacaaaccg gaggaaggtg   1200
gggatgacgt caaatcagca tgcccctgat gacctgggct acacacgtgc tacaatggtc   1260
gggacaacga gtagcgcgcc cgcgagggtt agctaatctc taaaaaccga tctcagttcg   1320
gattgcaggc tgcaactcgc ctgcatgaag ccggaatcgc tagtaatcgc ggatcagcat   1380
gccgcggtga atccgttccc gggccttgta cacaccgccc gtcacaccat gagagtttgt   1440
aacacccaaa gccggtgggg caacccttcg gggagctagc cgtctaaggt gggacagatg   1500
attggggtga agtcgtaaca aggtaa                                        1526

<210> SEQ ID NO 2
<211> LENGTH: 1526
<212> TYPE: DNA
<213> ORGANISM: Lactobacillus rennini
<220> FEATURE:
<223> OTHER INFORMATION: KG43(NITE ABP-309)

<400> SEQUENCE: 2
gtttgatcct ggctcaggac gaacgctggc ggcgtgccta atacatgcaa gtcgcacgca     60
caaccgttaa cctgatcctg cttgcaggtg acgttaatgg acgtgagtgg cggacgggtg    120
agtaacacgt gggtaaccaa ccctgaagcg ggggataacc tttggaaaca gaggctaata    180
ccgcatagtt tatcgcgacc tcctggtcgc aataataaag acggcttcgg ctgtcacttc    240
aggacagacc cgcggcgtat tagctagttg gtgggataaa ggcctaccaa ggcgatgata    300
cgtagccgac ctgagagggt aatcggccac attgggactg agacacggcc caaactccta    360
cgggaggcag cagtagggaa tcttccacaa tggacgcaag tctgatggag caacgccgcg    420
tgagtgaaga agggtttcgg ctcgtaaaac gctgttgttg gagaagaacc gggggtagag    480
taactgttat ccccttgacg gtatccaacc agaaagccac ggctaactac gtgccagcag    540
ccgcggtaat acgtaggtgg caagcgttgt ccggatttat tgggcgtaaa gcgagcgcag    600
gcggtttttt aagtctgatg tgaaagcctt cggcttaacc gaagaagggc atcagaaact    660
gagaagcttg aggacagaaa aggaaagtgg aactccatgt gtagcggtga aatgcgtaga    720
tatatggaag aacaccagtg gcgaaggcgg ctttctggtc tgttactgac gctgaggctc    780
gaaagtatgg ggagcgaaca ggattagata ccctggtagt ccataccgta aacgatgaat    840
gctaagtgtt ggagggtttc cgcccttcag tgctgcagct aacgcattaa gcattccgcc    900
tggggagtac gaccgcaagg ttgaaactca aaggaattga cggggcccg cacaagcggt    960 ggagcatgtg gtttaattcg aagcaacgcg aagaacctta ccaggtcttg acatcctttg   1020
accgctgtcg agacagtt tgcccttcgg ggccaaagtg acaggtggtg catggttgtc    1080
gtcagctcgt gtcgtgagat gttgggttaa gtcccgcaac gagcgcaacc cttatgacta   1140
gttgccagca tttagttggg cactctagtg agactgccgg tgacaaaccg gaggaaggtg   1200
gggatgacgt caaatcagca tgcccctgat gacctgggct acacacgtgc tacaatggtc   1260
gggacaacga gtagcgcgcc cgcgagggtt agctaatctc taaaaaccga tctcagttcg   1320
gattgcaggc tgcaactcgc ctgcatgaag ccggaatcgc tagtaatcgc ggatcagcat   1380
gccgcggtga atccgttccc gggccttgta cacaccgccc gtcacaccat gagagtttgt   1440
aacacccaaa gccggtgggg caacccttcg gggagctagc cgtctaaggt gggacagatg   1500
attggggtga agtcgtaaca aggtaa                                        1526
```

LACTIC ACID BACTERIUM CAPABLE OF PRODUCING γ-AMINOBUTYRIC ACID

TECHNICAL FIELD

The present invention relates to a lactic acid bacterium belonging to the genus *Lactobacillus*, which can produce γ-aminobutyric acid (to be referred to as "GABA" hereinafter) even under a condition wherein lactic acid exists in a medium at the time of commencement of culturing, and a method for producing a culture mixture comprising γ-aminobutyric acid using the same.

BACKGROUND OF THE INVENTION

GABA is an amino acid which is currently drawing attention since it has physiological effects such as a hypotensive effect, a diuretic effect and a tranquilizing effect. Since the food containing GABA is limited to some vegetable, tea, rice and the like and its content is also small, some methods for producing GABA using GABA fermenting lactic acid bacteria are proposed (e.g., see Patent References 1 to 3). As such GABA producing lactic acid bacteria, *Lactobacillus hilgardii*, *Lactococcus lactis* subspecies *cremoris*, *Lactococcus lactis* subspecies *lactis*, *Enterococcus casseliflavus*, *Lactobacillus brevis*, *Lactobacillus plantarum*, *Streptococcus thermophilus* and the like are known, which have the ability to produce GABA from L-glutamic acid or a salt of L-glutamic acid by decarboxylation reaction.

However, since these lactic acid bacteria require expensive components such as whey powder, skimmed milk, casein and peptone for the medium, the productivity from the viewpoint of cost is not good (e.g., see Patent Reference 1 or 4). Also, when soy sauce koji or gluten as an inexpensive material is degraded with an acid or degraded with an enzyme or koji, and the eluted glutamine is converted into glutamic acid by glutaminase to be used as the medium, the common salt generated by the neutralization or the common salt added as an antipollution countermeasure at the time of the enzymatic degradation inhibits the GABA production of lactic acid bacteria. Although several salinity tolerant GABA producing lactic acid bacteria have been reported, the optimum common salt concentration for GABA fermentation is a markedly high salinity of from 12.5 to 18% (e.g., see Patent Reference 5). When the promotion of a dietary life of intending hypochloric diet in order to avoid life style-related diseases is taken into consideration, the food and seasonings having high common salt content are not desirable. Additionally, since there is a side of expecting hypotensive activity from GABA, combination of it with high common salt concentration loses the original meaning.

Based on the above, for producing GABA by a lactic acid bacterium, although it is ideal to use inexpensive material such as koji and gluten by degrading it under a low common salt concentration, the low common salt concentration poses a problem of causing pollution by wild strains. The pollution occurs at an early stage of the culturing, and when an alcohol is produced or pH is lowered as a result, growth of the GABA producing lactic acid bacterium is inhibited. Therefore, sufficient amount of the object GABA cannot be obtained. As a means for preventing pollution by these wild strains at a low common salt concentration, there is a method which uses ethanol, acetic acid and lactic acid which are generally frequently used as food antiseptics. However, although ethanol and acetic acid suppress the contaminants, they also suppress the GABA producing lactic acid bacterium. On the other hand, since lactic acid bacteria produces lactic acid by themselves, they have higher resistance to lactic acid than other bacteria.

Accordingly, although the inventors of the present invention have considered about the use of lactic acid as antiseptics, there is a new problem that the GABA producing lactic acid bacterium cannot grow when lactic acid is added at the time of the commencement of culturing in the presence of common salt, or can grow but does not produce GABA.

Patent Reference 1: JP-A-2000-210075
Patent Reference 2: JP-A-2004-215529
Patent Reference 3: JP-A-2005-102559
Patent Reference 4: Japanese Patent No. 3426157
Patent Reference 5: Japanese Patent No. 2704493

DISCLOSURE OF THE INVENTION

Problems to be Solved by the Invention

The problems of the present invention is to provide a lactic acid bacterium which can produce GABA under a coexisting condition of lactic acid and common salt in the medium at time of commencement of culturing, and to provide a method for producing a culture mixture comprising GABA.

Means for Solving the Problems

With the aim of solving the above-mentioned problems, the inventors of the present invention have conducted intensive studies and found as a result that the problems can be solved by isolating a lactic acid bacterium from unrefined soy, which can produce GABA even under a coexisting condition of lactic acid and common salt at time of commencement of culturing and using it to accomplish the present invention.

Namely, the present invention relates to the following (1) to (4):

(1) A lactic acid bacterium belonging to the genus *Lactobacillus*, which can produce γ-aminobutyric acid under a coexisting condition of lactic acid and common salt in a medium at time of commencement of culturing;

(2) A lactic acid bacterium belonging to the genus *Lactobacillus*, which can produce γ-aminobutyric acid under a coexisting condition of from 1 to 4% of lactic acid and from 8 to 12% of common salt in a medium at time of commencement of culturing;

(3) The lactic acid bacterium according to the above (1) or (2), wherein the lactic acid bacterium is *Lactobacillus rennini*; and (4) A method for producing culture mixture comprising a γ-aminobutyric acid, wherein the lactic acid bacterium described in any one of the above (1) to (3) is cultured after inoculating into a medium containing L-glutamic acid and/or salts thereof.

Effect of the Invention

According to the present invention, a method for stably producing GABA using inexpensive materials without causing inhibition of the fermentation by wild strains can be provided.

BRIEF DESCRIPTION OF THE DRAWINGS

FIG. 1 shows a molecular genealogical tree of *Lactobacillus rennini* strains KG34, KG43, S1, KG31, KG64, KG-18-4 and KG4-14-1.

BEST MODE FOR CARRYING OUT THE INVENTION

The lactic acid bacterium concerned in the present invention is a strain belonging to the genus *Lactobacillus*, and for example, a lactic acid bacterium isolated from unrefined soy can be used. The lactic acid bacterium of the present invention has the ability to produce GABA under a coexisting condition of lactic acid and common salt in the medium at time of commencement of culturing, and can produce GABA under a coexisting condition of from 1 to 4% of lactic acid and from 8 to 12% of common salt. It is preferable that the lactic acid bacterium is *Lactobacillus rennini*, and examples of the lactic acid includes, *Lactobacillus rennini* strain KG34, *Lactobacillus rennini* strain KG43 and the like.

The *Lactobacillus rennini* strain KG34 was deposited on Feb. 7, 2006, in the National Institute of Technology and Evaluation (NITE), NITE Patent Microorganisms Depository (NPMD) (postal code 292-0818; 2-5-8, Kazusa Kamatari, Kisarazu, Chiba, Japan) (depository number NITE P-177), which was transferred to and accepted by the International Depository Authority on Sep. 1, 2006, under the Budapest Treaty (depository number NITE BP-177). All restrictions on public access to the deposited material will be irrevocably removed upon the grant of a patent on this application.

Also, the *Lactobacillus rennini* strain KG43 was deposited on Jan. 31, 2007, in the National Institute of Technology and Evaluation (NITE), NITE Patent Microorganisms Depository (NPMD) (postal code 292-0818; 2-5-8 Kazusa Kamatari, Kisarazu, Chiba, Japan) (depository number NITE BP-309), which was immediately transferred to and accepted by the International Depository Authority under the Budapest Treaty (acceptance number NITE ABP-309). All restrictions on public access to the deposited material will be irrevocably removed upon the grant of a patent on this application.

Isolation of a lactic acid bacterium from unrefined soy is carried out by the following method. Namely, 25 g of unrefined soy is subjected to the stomaching treatment, an appropriate amount of the thus obtained liquid is added to an MRS-SOYTONE medium (5.5% MRS broth, 0.5% Bactosoytone, 0.5% sodium glutamate, 8% common salt, 5% food additive lactic acid, pH 5.1) charged with Durham tube, and static culture is carried out at 30° C. A culture medium in which generation of gas in the Durham tube was confirmed is appropriately diluted with the MRS-SOYTONE medium, and spread on a MRS-SOYTONE agar medium followed by culturing at 30° C. for 7 days in AnaeroPack Kenki (Mitsubishi Gas Chemical Co., Inc.). The thus obtained single colonies are again inoculated into the MRS-SOYTONE medium charged with Durham tube, and the strains in which generation of gas was confirmed are selected.

Seven strains KG34, KG43, S1, KG31, KG64, KG-18-4 and KG4-14-1 were isolated by the above method. Among the 7 strains, bacteriological properties of both of the strains KG34 and KG43 were examined, and the results shown in Table 1. As a comparative control, data on *Lactobacillus rennini* DMSZ 20253 as the standard strain of *Lactobacillus rennini* were also described therein. It can be seen that the standard strain *Lactobacillus rennini* DMSZ 20253 does not produce GABA since it does not have the glutamic acid decarboxylation ability.

TABLE 1

| | | KG-34 | KG-43 | *L. rennini* DMSZ 20253 |
|---|---|---|---|---|
| 1. Sugar fermentation | Glucose | + | + | + |
| | Galactose | + | + | + |
| | Sorbose | − | − | − |
| | Sucrose | − | − | − |
| | Maltose | − | − | − |
| | Cellobiose | + | + | + |
| | Trehalose | − | − | − |
| | Lactose | − | − | + |
| | Melibiose | − | − | − |
| | Raffinose | − | − | − |
| | Melezitol | − | − | − |
| | Xylose | + | + | + |
| | D-arabinose | − | − | − |
| | L-arabinose | + | + | + |
| | Ribose | + | + | + |
| | Rhamnose | − | − | w |
| | Fructose | + | + | + |
| | Glycerol | − | − | − |
| | Erythritol | − | − | − |
| | Ribitol | − | − | − |
| | Mannitol | − | − | − |
| | Sorbitol | − | − | − |
| | Xylitol | − | − | − |
| | Inositol | − | − | − |
| | D-glucosamine | + | + | + |
| | N-acetyl-D-glucosamine | + | + | + |
| | Amygdalin | − | − | + |
| | Aesculin | − | − | − |
| 2. Growth temperature (° C.) | 5 | − | − | − |
| | 15 | − | w | − |
| | 20 | + | w | + |
| | 25 | + | + | + |
| | 30 | + | + | + |
| | 37 | + | + | + |
| | 40 | + | − | + |
| | 45 | − | − | − |
| 3. Halotolerance (%) | 5 | + | + | + |
| | 10 | + | + | + |
| | 11 | + | + | + |
| | 12 | + | + | w |
| | 13 | + | + | − |
| | 14 | w | w | − |
| | 15 | − | − | − |
| | 16 | − | − | − |
| 4. Initial pH | 4 | + | + | − |
| | 5 | + | + | + |
| | 6 | + | + | + |
| | 7 | + | + | + |
| | 8 | − | − | − |
| | 9 | − | − | − |
| 5. Decarboxylation ability | Glutamic acid | + | + | − |
| | Aspartic acid | − | − | − |
| | Lysine | − | − | − |
| | Ornithine | + | − | + |
| 6. Others | Gas generation from glucose | − | − | − |
| | Mobility | − | − | − |
| | Lactic acid optical rotation | D | D | D |
| | Ammonia formation from arginine | − | − | − |
| | Spore | − | − | − |
| | Catalase | − | − | − |
| | Diaminopimelic acid in cell wall | no | no | no |

*w: weak but +

Additionally, 16S rDNA (16S rDNA gene) complete nucleotide sequences of the lactic acid bacterium of the present invention *Lactobacillus rennini* strains KG34, KG43, S1, KG31, KG64, KG-18-4 and KG4-14-1 were determined by the following method.

Each of the lactic acid bacterium *Lactobacillus rennini* strains KG34, KG43, S1, KG31, KG64, KG-18-4 and KG4-14-1 was inoculated into an MRS-Soytone medium (MRS broth 5.5%, Soytone 0.5%, NaCl 8%, sodium glutamate 0.5%, pH 5.1) and cultured at 30° C. for 4 days. Gen-Torukun™ (for yeast) (Takara Bio) was used for the extraction of genomic DNA. Complete region of the 16S rDNA was divided into three fragments and amplified by PCR using the thus extracted genomic DNA as the template. By sequencing respective fragments and connecting them, complete region sequence was obtained. Takara Thermal Cycler MP was used as the thermal cycler, and ABI Prism 377 DNA Sequencer (Applied Biosystems) is used as the DNA sequencer. The thus obtained respective 16S rDNA nucleotide sequences are shown in SEQ ID NOs: 1 and 2.

Homology retrieval of species considered to be close relatives of the bacterium from the obtained 16S rDNA nucleotide sequences was carried out. A molecular genealogical tree was prepared by a neighborhood connecting method with the closely-related species using the 16S rDNA nucleotide sequences. Study of the closely-related species and assignment classification groups is carried out. As a result of retrieval by NCBI BLAST, the bacterium showed the highest homology (about 99.5%) with the 16S rDNA of *Lactobacillus rennini*, and formed the same cluster of *Lactobacillus rennini* in the genealogical tree. It was judged from the result that this bacterium is *Lactobacillus rennini*. The thus prepared genealogical tree is shown in FIG. 1.

Although the lactic acid bacterium of the present invention has the ability to produce GABA from L-glutamic acid or a salt of L-glutamic acid in the absence of common salt and lactic acid, it also can produce GABA even under a coexisting condition of from 1 to 4% of lactic acid and from 8 to 12% of common salt in the medium at time of commencement of culturing (see Example 2). Additionally, other than the time of the commencement of culturing, it can produce GABA under a coexisting condition of from 0 to 4% of lactic acid and from 0 to 12% of common salt in the medium.

The method of the present invention for producing a culture mixture comprising GABA is a method in which a culture mixture comprising GABA is produced by inoculating a lactic acid bacterium having the above-mentioned properties into a medium containing L-glutamic acid and/or salts thereof and culturing the same. As the lactic acid bacterium to be used in the present invention, although a species isolated from unrefined soy, cultured and sub-cultured is used, the same species contained in unrefined soy may be used as such or by newly isolating it. Additionally, any one of the freeze-dried cells, cryopreserved strain and liquid culture broth may be used.

It is necessary that the medium to be used in the present invention contains glutamic acid in order to produce GABA. As the glutamic acid to be contained in the medium, although L-glutamic acid as a kind of amino acid is chemically preferable, it may be any one of the glutamic acid or sodium glutamate as a food additive agent having the use as a seasoning, other glutamic acid salts, and further the glutamic acid obtained by hydrolyzing a food protein with an acid or enzyme. Additionally, foods which contain free glutamic acid such as a seasoning, a processed marine product and a tomato can be used as such. In this connection, when a culture mixture comprising further large amount of GABA is obtained, it is necessary to use a medium containing further large amount of glutamic acid.

Also, in addition to the above-mentioned glutamic acid, it is preferable for the growth of the lactic acid bacterium that the medium to be used in the present invention contains at least one of sugars such as glucose, fructose and maltose, food containing vitamins and minerals such as yeast extract and meat extract, or koji and koji digests. Additionally, food additives such as an emulsifying agent, a stabilizing agent and a pH adjusting agent can also be used. Examples of the koji and koji digests which can be used in the medium include protein hydrolyzates prepared by allowing a koji fungus to react with, or enzymes of the koji fungus to react with, one or two or more of denaturation-treated materials selected from cereals such as wheat, barley, rye, pearl barley, pressed wheat or barley, quinoa, Italian millet, Japanese millet, millet, rice and corn and beans such as soybean, adzuki bean, kidney bean, lupine bean, glass bean and lens bean. Soy sauce, unrefined soy, miso, protein hydrolyzates of beans and the like, and the like are preferable.

Inoculation of the lactic acid bacterium in the present invention is carried out by culturing the above-mentioned *Lactobacillus rennini* capable of producing GABA, at from 25 to 35° C. for from 48 to 96 hours using a medium containing a glutamic acid source, common salt and a carbon source and having an initial pH of from 4.0 to 7.0, and inoculating the resulting lactic acid bacterium seed culture in a volume of approximately from 1/1,000 to 1/10 based on the volume of the main culture medium.

Although the size and quality of the material of the device which can be used in the culturing of the present invention is not limited, as long as it can be washed and heat-sterilized and can be used for the production of food, it is preferable that it has such a hygienic structure that it can hardly be contaminated by sundry germs. Regarding the culture conditions, the culture temperature is from 20 to 40° C., preferably from 25 to 35° C., and the initial pH is preferably from 4.0 to 7.0, based on the bacteriological properties of the lactic acid bacterium (see Table 1). Regarding the culture period, it is necessary to carry out for such a sufficient period of time that glutamic acid source such as L-glutamic acid and/or salts thereof can be converted into the desired concentration of GABA. For example, a period of from 1 to 4 weeks is preferable.

In this manner, a culture mixture comprising GABA which has broad applications as raw materials of processed food and the like can be obtained. For example, it is possible also to use the culture mixture comprising GABA obtained by the method of the present invention as a GABA reinforcing material by directly addition to various seasonings and food and drink.

Additionally, it can also be used by increasing the GABA content by treating steps such as compression, filtration, concentration and drying. As the above-mentioned filtration step, it can be carried out using a general compression filtration apparatus for food processing use which uses filter, filter cloth or the like, and filter aid for food use such as diatomaceous earth, cellulose and activated carbon can be used. For the concentration step, apparatus such as a vacuum concentrator, a reduced-pressure concentrator, a distillation still and a freeze concentrator can be used, and a method in which moisture in the culture mixture is evaporated by simply heating can also be used. Also, as the drying step, it is preferable to carry out a spray drying or freeze drying by an efficient and hygienic method. Additionally, in order to obtain a culture mixture in which the GABA content was further increased, a liquid chromatography or the method can also be used in addition to the above-mentioned steps.

By treating the culture mixture comprising GABA in the manner, liquid or powder foodstuffs comprising GABA can be obtained. By formulating them into various food articles or carrying out their secondary processing, seasonings or food and drink wherein GABA is reinforced can be easily obtained. In the secondary processing, components generally used in food such as excipient, sweetener, thickener, protein, peptide, lipid, polysaccharides, sugar and salts can be contained.

In this connection, measurement of the GABA content in the thus obtained culture mixture and seasonings and food and drink supplemented with the culture mixture can be carried out using instruments for analysis such as a high performance liquid chromatography and an amino acid analyzer, an analytical reagent using enzyme(s) and the like.

Although the following describes the present invention further in detail with reference to examples, the present invention is not limited thereto.

EXAMPLES

Example 1

<Acquisition of Lactic Acid Bacterium>

Appropriate amounts of samples to be tested were collected from various kinds of fermented food, and an appropriate amount of each sample was added to an MRS-SOYTONE medium (5.5% MRS broth, 0.5% Bactosoytone, 0.5% sodium glutamate, 8% common salt, 5% food additive lactic acid, pH 5.1) charged with Durham tube, and static culture was carried out at 30° C. A culture medium in which generation of gas in the Durham tube was confirmed was appropriately diluted with the MRS-SOYTONE medium and spread on an MRS-SOYTONE agar medium and followed by culture at 30° C. for 7 days in AnaeroPack Kenki (Mitsubishi Gas Chemical Co., Inc.). The thus obtained single colonies were again inoculated into the MRS-SOYTONE medium charged with Durham tube, and GABA in the samples in which generation of gas was confirmed was measured. In this connection, the strains isolated from the same isolation source were subjected to individual identification in order to avoid selection of two or more of the same strain. GABA was measured by a high performance amino acid analyzer L-8800 manufactured by Hitachi, Ltd. As a result, it was revealed that the strains KG34, KG43, S1, KG31, KG64, KG-18-4 and KG4-14-1 were producing GABA. In this connection, physiological properties of the strain KG34 and strain KG43 are shown in Table 1, and 16S rDNA sequences of the strain KG34 and strain KG43 are shown in SEQ ID NOs:1 and 2. The 16S rDNA sequences of strain KG34 and strain KG43 coincided with each other 100%.

Example 2

<Confirmation of Salt Resistance and Lactic Acid Resistance>

Using a medium in which common salt was changed to 8% or 12%, and food additive lactic acid to 0%, 1% or 4%, based on an MRS-Soytone medium (5.5% MRS broth, 0.5% Soytone, 0.5% sodium glutamate, pH 5.1) charged with Durham tube, GABA productivities of the strains KG34, KG43, S1, KG31, KG64, KG-18-4 and KG4-14-1 were confirmed under such a condition that common salt and lactic acid are present in the medium at time of commencement of culture. Additionally, in that case, comparison with conventionally known GABA producing lactic acid bacteria was carried out, and the results are shown in Table 2.

TABLE 2

| | Lactic acid 0% | | Lactic acid 1% | | Lactic acid 4% | |
|---|---|---|---|---|---|---|
| Strains | Salt 8% | Salt 12% | Salt 8% | Salt 12% | Salt 8% | Salt 12% |
| L. hilgardii NBRC 15886 | x | x | x | x | x | x |
| La. lactis subsp. cremoris NBRC 100676 | Δ | Δ | x | x | x | x |
| La. lactis subsp. lactis NBRC 12007 | Δ | Δ | x | x | x | x |
| E. casseliflavus NBRC 100478 | Δ | Δ | x | x | x | x |
| L. kefiri NBRC 15888 | Δ | Δ | x | x | x | x |
| L. brevis IAM 1082 | Δ | Δ | Δ | Δ | x | x |
| L. brevis IAM 1318 | Δ | Δ | Δ | x | x | x |
| L. brevis IAM 10075 | Δ | Δ | Δ | x | x | x |
| L. brevis NBRC 3345 | Δ | Δ | x | x | x | x |
| L. brevis NBRC 3960 | Δ | Δ | x | x | x | x |
| L. brevis NBRC 12005 | Δ | Δ | x | x | x | x |
| L. brevis NBRC 12520 | Δ | Δ | x | x | x | x |
| L. brevis NBRC 13109 | Δ | Δ | x | x | x | x |
| L. brevis NBRC 13110 | Δ | Δ | x | x | x | x |
| L. plantarum NBRC 12006 | Δ | Δ | x | x | x | x |
| L. plantarum NBRC 12519 | Δ | Δ | x | x | x | x |
| S. thermophilus NBRC 13957 | Δ | Δ | x | x | x | x |
| L. rennini KG-34 | ○ | ○ | ○ | ○ | ○ | ○ |
| L. rennini KG-43 | ○ | ○ | ○ | ○ | ○ | ○ |
| L. rennini S1 | ○ | Δ | ○ | Δ | ○ | ○ |
| L. rennini KG-31 | ○ | ○ | ○ | ○ | ○ | Δ |
| L. rennini KG-64 | ○ | ○ | ○ | ○ | ○ | Δ |
| L. rennini KG-18-4 | Δ | Δ | ○ | ○ | ○ | Δ |
| L. rennini KG4-14-1 | ○ | ○ | ○ | ○ | ○ | Δ |

\* L.: Lactobacillus

La.: Lactococcus

E.: Enterococcus

S.: Streptococcus

\*\* ○: produces GABA

Δ: can grow but no GABA production x: no growth

Example 3

<Production Method of Culture Mixture (Seasoning) Comprising GABA>

By adding 160 ml of warm water to 70 g of wheat gluten and 100 g of soy koji and further adding thereto as glutaminase, 5 ml of a culture broth obtained by 36 hours of aeration-agitation culturing of *Candida famata* km-1 (FERM P-8897) (medium composition: glucose 6%, yeast extract 1%, potassium dihydrogenphosphate 0.1%, magnesium sulfate 0.1%, pH 5.5, culture temperature 30° C.), degradation of gluten and conversion of glutamine formed by the degradation into glutamic acid were carried out at 50° C. for 24 hours. After adding common salt to the thus obtained degradation product to be a final concentration of 8% and further adding food additive lactic acid to be a final concentration of 1% followed by lowering the temperature to be 30° C., *Lactobacillus rennini* strain KG34 or strain KG43 was inoculated to a density of about $10^6$ cells/ml and cultured at 30° C. for 7 days with gentle stirring. Each of the thus obtained culture mixtures was filtered to obtain a clear liquid. The GABA content of the culture liquid into which the strain KG34 was inoculated was 13.0 mg/ml, and 19.5 mg/ml in the case of KG43. As a control, although the same test was carried out using a conventionally known GABA producing strain *Lactobacillus brevis* NBRC 3345, the GABA concentration of the finally obtained clear liquid was 2.0 mg/ml. Therefore, sufficient GABA production was not carried out.

While the present invention has been described in detail and with reference to specific embodiments thereof, it will be apparent to one skilled in the art that various changes and modifications can be made therein without departing from the spirit and scope of the present invention.

This application is based on a Japanese patent application filed on Feb. 21, 2006 (Japanese Patent Application No. 2006-043836), the entire contents thereof being thereby incorporated by reference. All of the references cited herein are incorporated as a whole.

INDUSTRIAL APPLICABILITY

According to the present invention, a method for stably producing GABA using inexpensive materials without causing inhibition of the fermentation by wild strains can be provided.

The invention claimed is:

1. A lactic acid bacterium of the species *Lactobacillus Rennini*, which can produce γ-aminobutyric acid under a coexisting condition of from 1 to 4% of lactic acid and from 8 to 12% of common salt in a medium at time of commencement of culturing.

2. A method for producing culture mixture comprising a γ-aminobutyric acid, wherein the lactic acid bacterium described in claim 1 is cultured after inoculating into a medium containing L-glutamic acid and/or salts thereof.

* * * * *